(12) United States Patent
Dockal et al.

(10) Patent No.: US 8,022,187 B2
(45) Date of Patent: Sep. 20, 2011

(54) FVIII-INDEPENDENT FIX-MUTANT PROTEINS FOR HEMOPHILIA A TREATMENT

(75) Inventors: Michael Dockal, Vienna (AT); Rudolf Hartmann, Vienna (AT); Friedrich Scheiflinger, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 509 days.

(21) Appl. No.: 12/022,059

(22) Filed: Jan. 29, 2008

(65) Prior Publication Data

US 2008/0214461 A1    Sep. 4, 2008

Related U.S. Application Data

(60) Provisional application No. 60/898,877, filed on Feb. 1, 2007.

(51) Int. Cl.
*A61K 35/14* (2006.01)
*A61K 38/36* (2006.01)
*C07K 14/745* (2006.01)

(52) U.S. Cl. ..................... 530/384; 514/13.7
(58) Field of Classification Search .................. None
See application file for complete search history.

(56) References Cited

U.S. PATENT DOCUMENTS 6,531,298 B2    3/2003    Stafford et al.

FOREIGN PATENT DOCUMENTS

WO    WO 02/40544 A2    5/2002

OTHER PUBLICATIONS

Christophe, Olivier D. et al., "Blood Coagulation Factor IX Residues Glu[78] and Arg[94] Provide a Link between Both Epidermal Growth Factor-like Domains That Is Crucial in the Interaction with Factor VIII Light Chain," 1998, *The Journal of Biologcial Chemistry*; vol. 273, No. 1, p. 222-227.
Hartmann, Rudolf et al., "Variants of Recombinant Factor IX with Enhanced Functional Properties," 2007, *Blood*, vol. 110, No. 11, Part 1, p. 791A; Abstract of the 49th Annual Meeting of the American Society of Hematology, Atlanta, Dec. 8-11, 2007.
Kolkman, Joost A., et al., "Insertion Loop 256-268 in Coagulation Factor IX Restricts Enzymatic Activity in the Absence but Not in the Presence of Factor VIII," 2000, *Biochemistry*; vol. 39, p. 7398-7405.
Chang, Jinli, et al., "Changing Residue 338 in Human Factor IX from Arginine to Alanine Causes an Increase in Catalytic Activity;" May 15, 1998; *The Journal of Biological Chemistry*; vol. 273; No. 20; pp. 12089-12094.
Hopfner, Karl-Peter, et al., "Coagulation factor 1Xa: the relaxed conformation of Tyr99 blocks substrate binding:" Jan. 20, 1999; *Structure*; vol. 7; pp. 989-996.
Hopfner, Karl-Peter, et al., "Converting blood coagulation factor 1Xa into factor Xa: dramatic increase in amidolytic activity identifies important active site determinants;" 1997; *The EMBO Journal*; vol. 16; No. 22; pp. 6626-6635.
Sichler, Katrin, "Physiological f1Xa Activation Involves a Cooperative Conformational Rearrangement of the 99-Loop;" Feb. 7, 2003; *The Journal of Biological Chemistry*; vol. 278; No. 6; pp. 4121-4126.

*Primary Examiner* — Marsha Tsay
(74) *Attorney, Agent, or Firm* — Kilpatrick Townsend & Stockton LLP

(57) ABSTRACT

The present invention relates to recombinant blood coagulation factor IX (rFIX) mutants having factor VIII (FVIII) independent factor X (FX) activation potential. Five full length FIX proteins with combinations of mutations of amino acids important for functional activity of FIX and FIX wild type were cloned and expressed in HEK 293 cells. The proteins were tested by an activated partial thromboplastin time (aPTT) assay in FVIII-depleted plasma as well as in FVIII-inhibited patient plasma. In FVIII-depleted plasma functional activity of the FIX mutants was calculated as increased FVIII equivalent activity. The mutant proteins had increased FVIII equivalent activity. In FVIII-inhibited patient plasma the FEIBA equivalent activity was calculated for analysis of FVIII independent FX activation potential. The proteins had also increased FEIBA equivalent activity. Furthermore, the pre-activated FIX proteins had an increased activity in FIX-depleted plasma containing FVIII inhibitors. Therefore these FIX mutants are alternatives as bypassing agents for treatment of FVIII inhibitor patients.

10 Claims, 6 Drawing Sheets

SEQUENCE LISTING

<160> NUMBER OF SEQ ID NOS: 20

<210> SEQ ID NO 1
<211> LENGTH: 1386
<212> TYPE: DNA
<213> ORGANISM: Homo sapiens
<220> FEATURE:
<223> OTHER INFORMATION: nucleic acid encoding blood coagulation factor
      IX (rFIX)

<400> SEQUENCE: 1

```
atgcagcgcg tgaacatgat catggcagaa tcaccaggcc tcatcaccat ctgcctctta      60
ggatatctac tcagtgctga atgtacagtt tttcttgatc atgaaaacgc aacaaaatt     120 ctgaatcggc caaagaggta taattcaggt aaattggaag agtttgttca agggaacctt    180
gagagagaat gtatggaaga aaagtgtagt tttgaagaag cacgagaagt ttttgaaaac    240
actgaaagaa caactgaatt ttggaagcag tatgttgatg gagatcagtg tgagtccaat    300
ccatgtttaa atggcggcag ttgcaaggat gacattaatt cctatgaatg ttggtgtccc    360
tttggatttg aaggaaagaa ctgtgaatta gatgtaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccatttcc atgtggaaga    540
gtttctgttt cacaaacttc taagctcacc cgtgctgagg ctgtttttcc tgatgtggac    600
tatgtaaatt ctactgaagc tgaaaccatt ttggataaca tcactcaaag cacccaatca    660
tttaatgact tcactcgggt tgttggtgga gaagatgcca aaccaggtca attcccttgg    720
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
```

```
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac cccatgttac tgaagtggaa   1260
gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
acttaa                                                              1386

<210> SEQ ID NO 2
<211> LENGTH: 461
<212> TYPE: PRT
<213> ORGANISM: Homo sapiens
<220> FEATURE:
<223> OTHER INFORMATION: wildtype blood coagulation factor IX (rFIX)
      protein

<400> SEQUENCE: 2

Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
```

```
                 260              265                  270
Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
450                 455                 460

<210> SEQ ID NO 3
<211> LENGTH: 1389
<212> TYPE: DNA
<213> ORGANISM: Artificial Sequence
<220> FEATURE:
<223> OTHER INFORMATION: nucleic acid encoding recombinant blood
      coagulation factor IX (rFIX) mutant FIX-Y94F/K98T

<400> SEQUENCE: 3
atgcagcgcg tgaacatgat catggcagaa tcaccaggcc tcatcaccat ctgcctctta      60
ggatatctac tcagtgctga atgtacagtt tttcttgatc atgaaaacgc aacaaaatt     120 ctgaatcggc caagaggta taattcaggt aaattggaag agtttgttca agggaacctt     180
gagagagaat gtatggaaga aaagtgtagt tttgaagaag cacgagaagt ttttgaaaac     240
actgaaagaa caactgaatt tggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgagg ctgttttccc tgatgtggac     600
tatgtaaatt ctactgaagc tgaaaccatt ttggataaca tcactcaaag cacccaatca     660
tttaatgact tcactcgggt tgttggtgga agagatgcca aaccaggtca attcccttgg     720
caggttgttt tgaatggtaa agttgatgca ttctgtggag gctctatcgt taatgaaaaa     780
tggattgtaa ctgctgccca ctgtgttgaa actggtgtta aattacagtt gtcgcaggt     840 gaacataata ttgaggagac agaacataca gagcaaaagc gaaatgtgat tcgaattatt     900
cctcaccaca acttcaatgc agctattaat acctacaacc atgacattgc ccttctggaa     960
```

```
ctggacgaac ccttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaatga                                                           1389
```

<210> SEQ ID NO 4
<211> LENGTH: 461
<212> TYPE: PRT
<213> ORGANISM: Artificial Sequence
<220> FEATURE:
<223> OTHER INFORMATION: recombinant blood coagulation factor IX (rFIX) mutant FIX-Y94F/K98T

<400> SEQUENCE: 4

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
```

```
                275                 280                 285
His Thr Glu Gln Lys Arg Asn Val Ile Arg Ile Pro His His Asn
        290                 295                 300
Phe Asn Ala Ala Ile Asn Thr Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
                340                 345                 350
Val Ser Gly Trp Gly Arg Val Phe His Lys Gly Arg Ser Ala Leu Val
                355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
                420                 425                 430
Glu Glu Cys Ala Met Lys Gly Lys Tyr Gly Ile Tyr Thr Lys Val Ser
                435                 440                 445
Arg Tyr Val Asn Trp Ile Lys Glu Lys Thr Lys Leu Thr
        450                 455                 460

<210> SEQ ID NO 5
<211> LENGTH: 1389
<212> TYPE: DNA
<213> ORGANISM: Artificial Sequence
<220> FEATURE:
<223> OTHER INFORMATION: nucleic acid encoding recombinant blood
      coagulation factor IX (rFIX) mutant
      FIX-Y94F/K98T/Y177F

<400> SEQUENCE: 5
atgcagcgcg tgaacatgat catggcagaa tcaccaggcc tcatcaccat ctgcctctta      60
ggatatctac tcagtgctga atgtacagtt tttcttgatc atgaaaacgc caacaaaatt     120
ctgaatcggc caaagaggta taattccagg aaattggaag agtttgttca agggaacctt     180
gagagagaat gtatggaaga aaagtgtagt tttgaagaag cacgagaagt ttttgaaaac     240
actgaaagaa caactgaatt ttggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgagg ctgttttcc tgatgtggac     600 tatgtaaatt ctactgaagc tgaaaccatt ttggataaca tcactcaaag cacccaatca     660
tttaatgact tcactcgggt tgttggtgga gaagatgcca aaccaggtca attcccttgg     720
caggttgttt tgaatggtaa agttgatgca ttctgtggag gctctatcgt taatgaaaaa     780
tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca acttcaatgc agctattaat acctacaacc atgacattgc ccttctggaa     960
ctggacgaac ccttagtgct aaacagctac gttacaccta tttgcattgc tgacaaggaa    1020
```

```
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tttaacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaatga                                                            1389
```

<210> SEQ ID NO 6
<211> LENGTH: 461
<212> TYPE: PRT
<213> ORGANISM: Artificial Sequence
<220> FEATURE:
<223> OTHER INFORMATION: recombinant blood coagulation factor IX (rFIX) mutant FIX-Y94F/K98T/Y177F

<400> SEQUENCE: 6

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285
```

```
His Thr Glu Gln Lys Arg Asn Val Ile Arg Ile Ile Pro His His Asn
        290                 295                 300
Phe Asn Ala Ala Ile Asn Thr Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
    370                 375                 380
Ser Thr Lys Phe Thr Ile Phe Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr
    450                 455                 460

<210> SEQ ID NO 7
<211> LENGTH: 1389
<212> TYPE: DNA
<213> ORGANISM: Artificial Sequence
<220> FEATURE:
<223> OTHER INFORMATION: nucleic acid encoding recombinant blood
      coagulation factor IX (rFIX) mutant
      FIX-Y94F/A95aK/K98T/Y177F

<400> SEQUENCE: 7
atgcagcgcg tgaacatgat catggcagaa tcaccaggcc tcatcaccat ctgcctctta      60
ggatatctac tcagtgctga atgtacagtt tttcttgatc atgaaaacgc caacaaaatt     120
ctgaatcggc caaagaggta taattcaggt aaattggaag agtttgttca gggaaccctt     180
gagagagaat gtatggaaga aaagtgtagt tttgaagaag cacgagaagt ttttgaaaac     240
actgaaagaa caactgaatt tggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgagg ctgttttcc tgatgtggac     600 tatgtaaatt ctactgaagc tgaaaccatt ttggataaca tcactcaaag cacccaatca     660
tttaatgact tcactcgggt tgttggtgga aagatgcca aaccaggtca attcccttgg     720
caggttgttt tgaatggtaa agttgatgca ttctgtggag ctctatcgt taatgaaaaa     780 tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca acttcaataa ggctattaat acctacaacc atgacattgc ccttctggaa     960
ctggacgaac cctagtgct aaacagctac gttacaccta tttgcattgc tgacaaggaa    1020
tacacgaaca tcttcctcaa atttggatct ggctatgtaa gtggctgggg aagagtcttc    1080
```

```
cacaaaggga gatcagcttt agttcttcag taccttagag ttccacttgt tgaccgagcc    1140
acatgtcttc gatctacaaa gttcaccatc tttaacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaatga                                                           1389
```

<210> SEQ ID NO 8
<211> LENGTH: 461
<212> TYPE: PRT
<213> ORGANISM: Artificial Sequence
<220> FEATURE:
<223> OTHER INFORMATION: recombinant blood coagulation factor IX (rFIX) mutant FIX-Y94F/A95aK/K98T/Y177F

<400> SEQUENCE: 8

```
Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr Val Phe Leu
                 20                  25                  30

Asp His Glu Asn Ala Asn Lys Ile Leu Asn Arg Pro Lys Arg Tyr Asn
             35                  40                  45

Ser Gly Lys Leu Glu Glu Phe Val Gln Gly Asn Leu Glu Arg Glu Cys
         50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300
```

Phe Asn Lys Ala Ile Asn Thr Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
        340                 345                 350

Val Ser Gly Trp Gly Arg Val Phe His Lys Gly Arg Ser Ala Leu Val
    355                 360                 365

Leu Gln Tyr Leu Arg Val Pro Leu Val Asp Arg Ala Thr Cys Leu Arg
370                 375                 380

Ser Thr Lys Phe Thr Ile Phe Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 9
<211> LENGTH: 1389
<212> TYPE: DNA
<213> ORGANISM: Artificial Sequence
<220> FEATURE:
<223> OTHER INFORMATION: nucleic acid encoding recombinant blood
      coagulation factor IX (rFIX) mutant
      FIX-Y94F/K98T/Y177F/I213V/E219G

<400> SEQUENCE: 9

| | | |
|---|---|---|
| atgcagcgcg tgaacatgat catggcagaa tcaccaggcc tcatcaccat ctgcctctta | 60 |
| ggatatctac tcagtgctga atgtacagtt tttcttgatc atgaaaacgc aacaaaatt | 120 |
| ctgaatcggc aaagaggta taattcaggt aaattggaag agtttgttca agggaacctt | 180 |
| gagagagaat gtatggaaga aaagtgtagt tttgaagaag cacgagaagt ttttgaaaac | 240 |
| actgaaagaa caactgaatt tggaagcag tatgttgatg agatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccattcc atgtggaaga | 540 |
| gtttctgttt cacaaacttc taagctcacc cgtgctgagg ctgttttcc tgatgtggac | 600 |
| tatgtaaatt ctactgaagc tgaaaccatt ttggataaca tcactcaaag cacccaatca | 660 |
| tttaatgact tcactcgggt tgttggtgga gaagatgcca aaccaggtca attcccttgg | 720 |
| caggttgttt tgaatggtaa agttgatgca ttctgtggag ctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca acttcaatgc agctattaat acctacaacc atgacattgc ccttctggaa | 960 |
| ctggacgaac ccttagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga gatcagcttt agttcttcag taccttagag ttccacttgt tgaccgagcc | 1140 |

```
acatgtcttc gatctacaaa gttcaccatc tttaacaaca tgttctgtgc tggcttccat    1200
gaaggaggta gagattcatg tcaaggagat agtgggggac cccatgttac tgaagtggaa    1260
gggaccagtt tcttaactgg aattgtgagc tggggtgaag ctgtgcaat gaaaggcaaa     1320 tatggaatat ataccaaggt atcccggtat gtcaactgga ttaaggaaaa aacaaagctc    1380
acttaatga                                                           1389
```

<210> SEQ ID NO 10
<211> LENGTH: 461
<212> TYPE: PRT
<213> ORGANISM: Artificial Sequence
<220> FEATURE:
<223> OTHER INFORMATION: recombinant blood coagulation factor IX (rFIX) mutant FIX-Y94F/K98T/Y177F/I213V/E219G

<400> SEQUENCE: 10

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Phe Asn Ala Ala Ile Asn Thr Tyr Asn His Asp Ile Ala Leu Leu Glu
```

| | | 305 | | | | 310 | | | | 315 | | | | 320 | |
|---|---|---|---|---|---|---|---|---|---|---|---|---|---|---|---|

Leu Asp Glu Pro Leu Val Leu Asn Ser Tyr Val Thr Pro Ile Cys Ile
             325                   330                   335

Ala Asp Lys Glu Tyr Thr Asn Ile Phe Leu Lys Phe Gly Ser Gly Tyr
             340                   345                   350

Val Ser Gly Trp Gly Arg Val Phe His Lys Gly Arg Ser Ala Leu Val
        355                   360                   365

Leu Gln Tyr Leu Arg Val Pro Leu Val Asp Arg Ala Thr Cys Leu Arg
    370                   375                   380

Ser Thr Lys Phe Thr Ile Phe Asn Asn Met Phe Cys Ala Gly Phe His
385                   390                   395                   400

Glu Gly Gly Arg Asp Ser Cys Gln Gly Asp Ser Gly Gly Pro His Val
             405                   410                   415

Thr Glu Val Glu Gly Thr Ser Phe Leu Thr Gly Ile Val Ser Trp Gly
        420                   425                   430

Glu Gly Cys Ala Met Lys Gly Lys Tyr Gly Ile Tyr Thr Lys Val Ser
    435                   440                   445

Arg Tyr Val Asn Trp Ile Lys Glu Lys Thr Lys Leu Thr
    450                   455                   460

<210> SEQ ID NO 11
<211> LENGTH: 1389
<212> TYPE: DNA
<213> ORGANISM: Artificial Sequence
<220> FEATURE:
<223> OTHER INFORMATION: nucleic acid encoding recombinant blood
     coagulation factor IX (rFIX) mutant
     FIX-Y94F/A95aK/K98T/Y177F/I213V/E219G

<400> SEQUENCE: 11

```
atgcagcgcg tgaacatgat catggcagaa tcaccaggcc tcatcaccat ctgcctctta      60
ggatatctac tcagtgctga atgtacagtt tttcttgatc atgaaaacgc aacaaaatt     120 ctgaatcggc caaagaggta taattcaggt aaattggaag agtttgttca agggaacctt     180
gagagagaat gtatggaaga aaagtgtagt tttgaagaag cacgagaagt ttttgaaaac     240
actgaaagaa caactgaatt ttggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgagg ctgttttcc tgatgtggac     600 tatgtaaatt ctactgaagc tgaaaccatt ttggataaca tcactcaaag cacccaatca     660
tttaatgact tcactcgggt tgttggtgga agatgccaa accaggtca attcccttgg     720 caggttgttt tgaatggtaa agttgatgca ttctgtggag gctctatcgt taatgaaaaa     780
tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca acttcaataa ggctattaat acctacaacc atgacattgc ccttctggaa     960
ctggacgaac ccttagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccactgt tgaccgagcc    1140 acatgtcttc gatctacaaa gttcaccatc tttaacaaca tgttctgtgc tggcttccat    1200
```

```
gaaggaggta gagattcatg tcaaggagat agtgggggac cccatgttac tgaagtggaa    1260
gggaccagtt tcttaactgg aattgtgagc tggggtgaag gctgtgcaat gaaaggcaaa    1320
tatggaatat ataccaaggt atcccggtat gtcaactgga ttaaggaaaa aacaaagctc    1380
acttaatga                                                            1389
```

<210> SEQ ID NO 12
<211> LENGTH: 461
<212> TYPE: PRT
<213> ORGANISM: Artificial Sequence
<220> FEATURE:
<223> OTHER INFORMATION: recombinant blood coagulation factor IX (rFIX) mutant FIX-Y94F/A95aK/K98T/Y177F/I213V/E219G

<400> SEQUENCE: 12

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Phe Asn Lys Ala Ile Asn Thr Tyr Asn His Asp Ile Ala Leu Leu Glu
305                 310                 315                 320
```

| | | | | | | | | | | | |
|---|---|---|---|---|---|---|---|---|---|---|---|
| Leu | Asp | Glu | Pro | Leu | Val | Leu | Asn | Ser | Tyr | Val | Thr | Pro | Ile | Cys | Ile |
| | | | 325 | | | | 330 | | | | 335 |

Ala Asp Lys Glu Tyr Thr Asn Ile Phe Leu Lys Phe Gly Ser Gly Tyr
           340                    345                    350

Val Ser Gly Trp Gly Arg Val Phe His Lys Gly Arg Ser Ala Leu Val
      355                    360                    365

Leu Gln Tyr Leu Arg Val Pro Leu Val Asp Arg Ala Thr Cys Leu Arg
 370                   375                    380

Ser Thr Lys Phe Thr Ile Phe Asn Asn Met Phe Cys Ala Gly Phe His
385                  390                    395                  400

Glu Gly Gly Arg Asp Ser Cys Gln Gly Asp Ser Gly Gly Pro His Val
           405                    410                    415

Thr Glu Val Glu Gly Thr Ser Phe Leu Thr Gly Ile Val Ser Trp Gly
           420                    425                    430

Glu Gly Cys Ala Met Lys Gly Lys Tyr Gly Ile Tyr Thr Lys Val Ser
           435                    440                    445

Arg Tyr Val Asn Trp Ile Lys Glu Lys Thr Lys Leu Thr
     450                    455                    460

```
<210> SEQ ID NO 13
<211> LENGTH: 45
<212> TYPE: DNA
<213> ORGANISM: Artificial Sequence
<220> FEATURE:
<223> OTHER INFORMATION: Y94F-K98T mutant sense primer

<400> SEQUENCE: 13
cctcaccaca acttcaatgc agctattaat acctacaacc atgac          45

<210> SEQ ID NO 14
<211> LENGTH: 45
<212> TYPE: DNA
<213> ORGANISM: Artificial Sequence
<220> FEATURE:
<223> OTHER INFORMATION: Y94F-K98T mutant antisense primer

<400> SEQUENCE: 14
gtcatggttg taggtattaa tagctgcatt gaagttgtgg tgagg          45

<210> SEQ ID NO 15
<211> LENGTH: 45
<212> TYPE: DNA
<213> ORGANISM: Artificial Sequence
<220> FEATURE:
<223> OTHER INFORMATION: Y94F-A95aK-K98T mutant sense primer

<400> SEQUENCE: 15
cctcaccaca acttcaataa ggctattaat acctacaacc atgac          45

<210> SEQ ID NO 16
<211> LENGTH: 45
<212> TYPE: DNA
<213> ORGANISM: Artificial Sequence
<220> FEATURE:
<223> OTHER INFORMATION: Y94F-A95aK-K98T mutant antisense primer

<400> SEQUENCE: 16
gtcatggttg taggtattaa tagccttatt gaagttgtgg tgagg          45

<210> SEQ ID NO 17
<211> LENGTH: 24
<212> TYPE: DNA
<213> ORGANISM: Artificial Sequence
```

```
<220> FEATURE:
<223> OTHER INFORMATION: Y177F mutant sense primer

<400> SEQUENCE: 17
caccatcttt aacaacatgt tctg                                              24

<210> SEQ ID NO 18
<211> LENGTH: 24
<212> TYPE: DNA
<213> ORGANISM: Artificial Sequence
<220> FEATURE:
<223> OTHER INFORMATION: Y177F mutant antisense primer

<400> SEQUENCE: 18
cagaacatgt tgttaaagat ggtg                                              24

<210> SEQ ID NO 19
<211> LENGTH: 41
<212> TYPE: DNA
<213> ORGANISM: Artificial Sequence
<220> FEATURE:
<223> OTHER INFORMATION: I213V-E219G mutant sense primer

<400> SEQUENCE: 19
ctggaattgt gagctggggt gaaggctgtg caatgaaagg c                           41

<210> SEQ ID NO 20
<211> LENGTH: 41
<212> TYPE: DNA
<213> ORGANISM: Artificial Sequence
<220> FEATURE:
<223> OTHER INFORMATION: I213V-E219G mutant antisense primer

<400> SEQUENCE: 20
gcctttcatt gcacagcctt caccccagct cacaattcca g                           41
```

US 8,022,187 B2

FVIII-INDEPENDENT FIX-MUTANT PROTEINS FOR HEMOPHILIA A TREATMENT

CROSS-REFERENCES TO RELATED APPLICATIONS

This application claims benefit of U.S. Provisional Application No. 60/898,877, filed Feb. 1, 2007, the disclosure of which is hereby incorporated by reference in its entirety for all purposes.

FIELD OF THE INVENTION

The present invention relates to recombinant blood coagulation factor IX (rFIX) mutants having factor VIII (FVIII) independent factor X (FX) activation potential, cell cultures expressing rFIX mutants, a pharmaceutical composition for treating a bleeding disorder comprising said rFIX mutants, and a method for treating a bleeding disorder comprising the step of administering said rFIX mutants to a patient in need thereof.

BACKGROUND OF THE INVENTION

The blood coagulation cascade involves a series of serine protease enzymes (zymogens) and protein cofactors. When required, an inactive zymogen precursor is converted into the active form, which consequently converts the next enzyme in the cascade.

The cascade is divided into three distinct segments: the intrinsic, extrinsic, and common pathways (Schenone et al., Curr Opin Hematol. 2004; 11:272-7). The activation of factor X (FX) is the common point of the intrinsic and extrinsic pathways. The activation occurs either by the extrinsic complex formed by activated factor VII (FVIIa) and tissue factor, or by the intrinsic tenase complex composed of activated Factor IXa (FIXa) and activated Factor VIIIa (FVIIIa) (Mann, Thromb. Haemostasis 1999; 82:165-74).

Activated FX along with phospholipids, calcium, and factor Va (FVa) then converts prothrombin to thrombin (prothrombinase complex), which in turn cleaves fibrinogen to fibrin monomers. The monomers polymerize to form fibrin strands. Factor XIIIa (FXIIIa) covalently bonds these strands to one another to form a rigid mesh.

Deficiencies of the components of the intrinsic tenase complex, FVIIIa and FIXa, lead to severe bleeding disorders, hemophilia A and B, respectively. Hemophilia A is considered the classic form of hemophilia, whereas hemophilia B is also known as Christmas disease. Hemophilia A and B are the consequence of congenital deficiencies of FVIII and FIX, respectively. The worldwide incidence of hemophilia A is approximately 1 case per 5,000 male individuals and of hemophilia B 1 case per 30,000.

Originally patients with severe hemophilia had a shortened lifespan and diminished quality of life that was greatly affected by hemophilic arthropathy. But life expectancy has increased from 11 years before the 1960s for patients who were severely affected to more than 50-60 years by the early 1980s. This has been accomplished through the widespread use of replacement therapy.

Nowadays the treatment of choice for the management of hemophilia A is replacement therapy with various plasma derived or recombinant FVIII concentrates. Although progress in the production of FVIII to ensure purity, efficacy and viral safety has been made over the past decades, some limitations remain. First of all, severe hemophilia A patients are frequently affected by anti-FVIII inhibitor antibody formation, thus rendering the therapy ineffective. Approximately 30% of patients with severe hemophilia A develop alloantibody inhibitors that can neutralize FVIII (Hay, Haemophilia 2006; 12 Suppl 6:23-9, Peerlinck and Hermans, Haemophilia 2006; 12:579-90). Furthermore, acquired hemophilia may occur which is the development of FVIII antibody inhibitors in persons without a history of FVIII deficiency.

Attempts to overwhelm the inhibitors with large doses of human FVIII have been tried. Also porcine FVIII which has low cross-reactivity with human FVIII antibody has been administered. More frequently, FVIII-bypassing agents, including FEIBA (factor eight inhibitor bypassing activity), FIX complex and FVIIa have also been used.

Modification of the functional activity of the tenase complex would also be an elegant approach to address several of the above discussed issues in hemophilia treatment, i.e., deficiency of FVIII or FIX and inhibitor development.

In the tenase complex FIXa has critical importance (Rawala-Sheikh et al., Biochemistry 1990; 29:2606-11). FIXa is a two-chain vitamin K-dependent serine protease capable of hydrolysing the Arg194-Ile195 peptide bond in the FX molecule which leads to its activation (Venkateswarlu et al., Biophys. J. 2002; 82:1190-206). Although this reaction can proceed slowly in solution, it is significantly accelerated in the presence of negatively charged phospholipid surfaces. In vivo, these surfaces are mainly provided by activated platelets and plasma lipoproteins. The rate of the reaction is increased further by the presence of FVIIIa.

FIXa exhibits very low catalytic activity in an in vitro system lacking either the co-factor FVIIIa or the physiologic substrate FX. This is in contrast to the closest related homologue, FXa, which shows significant activity towards peptide substrates (in addition to its physiologic substrate prothrombin), independent of its co-factor protein FVa. Thus the drawback of the sophisticated regulation of this enzymatic system is that failure of a single component such as FVIIIa or the development of inhibitors suffices to interrupt the functional activity of the tenase apparatus.

An improved FIX protein, which has improved FVIII-independent FX activation potential could avoid this issue. Several amino acid residues of FIXa are already known to be important for regulation of enzymatic activity and interaction with both FVIIIa and FX.

The surface loop 99 of FIXa is important for regulation of FIXa activity (Hopfner et al., Structure Fold Des. 1999; 7:989-96). In the non-complexed FIXa this loop is stabilized in an inactive conformation and limits access of substrate to the catalytic machinery.

The mutations Y94F and K98T are located on the 99-loop, known to contribute to FX substrate binding by forming of the recognition site of the S2 and S4 pockets of FX. Y177F mimics the effect of activation by FVIIIa. Tyrosin 177 locks the 99-loop in an inactive conformation, which is released by binding of FVIIIa to FIXa (Sichler et al., J Biol Chem. 2003; 278:4121-26).

Val 213 and Gly 219 are conserved amino acids in most other trypsin-like proteases, and a double mutant of truncated FIX (I213V-E219G) expressed in *E. coli* showed increased amidolytic activity of FIXa (Hopfner et al., EMBO J. 1997; 16:6626-35).

However, in none of these publications full length FIX mutants expressed in mammalian cells showed an improved functional activity in a meaningful activated partial thromboplastin time (aPTT) assay in FVIII-depleted plasma or FVIII-inhibitor-patient plasma.

Thus, there remains a great need in the art for compositions and methods that provide an improved FIX molecule that can be used for treatment of patients with hemophilia A.

It was the inventive task of the present invention to develop novel FIX proteins by introduction of amino acid exchanges, which have improved FVIII-independent FX activation potential with coagulation FVIII activity useful for the treatment of bleeding disorders.

BRIEF SUMMARY OF THE INVENTION

The present invention relates to recombinant blood coagulation factor IX (rFIX) mutants having factor VIII (FVIII) independent factor X (FX) activation potential. Five full length FIX proteins with novel combinations of mutations of amino acids important for functional activity of FIX, i.e. SEQ ID NO:4 (FIX-Y94F/K98T), SEQ ID NO:6 (FIX-Y94F/K98T/Y177F), SEQ ID NO:8 (FIX-Y94F/A95aK/K98T/Y177F), SEQ ID NO:10 (FIX-Y94F/K98T/Y177F/I213V/E219G) and SEQ ID NO:12 (FIX-Y94F/A95aK/K98T/Y177F/I213V/E219G) and SEQ ID NO:2 (FIX wild type) were cloned, expressed in HEK 293 and purified by a three step purification protocol using anion exchange chromatography, pseudo-affinity chromatography and affinity chromatography. Pre-activated FIX was removed with biotinylated chloromethylketones and streptavidine-sepharose. Among other assays the proteins were tested by an activated partial thromboplastin time (aPTT) assay in FVIII-depleted plasma as well as FVIII-inhibited patient plasma. In FVIII-depleted plasma functional activity of a rFIX mutant was calculated as increased FVIII equivalent activity. PdFIX and FIX-WT had no or only a minor FVIII equivalent activity. From the 5 mutated proteins (at 5 µg/mL) FIX-Y94F/K98T and FIX-Y94F/A95aK/K98T/Y177F/I213V/E219G had the greatest effect with 14.7 and 16 FVIII equivalent mU/mL, and FIX-Y94F/K98T/Y177F/I213V/E219G resulted in 12 FVIII equivalent mU/mL. In FVIII-inhibited patient plasma the FEIBA equivalent activity was calculated for analysis of FVIII independent FX activation potential. PdFIX and FIX-WT had no or only a minor FEIBA equivalent activity. The best rFIX mutant FIX-Y94F/A95aK/K98T/Y177F/I213V/E219G showed a FEIBA equivalent activity of 162 mU/mL, FIX-Y94F/K98T and FIX-Y94F/K98T/Y177F/I213V/E219G had both approximately 115 FEIBA equivalent mU/mL. After pre-activation the rFIX proteins were tested in FIX-depleted plasma containing inhibitors. At 1 µg/mL FIXa-Y94F/K98T/Y177F/I213V/E219G displayed 73.4 times the activity of pdFIXa, whereas FIXa-Y94F/A95aK/K98T/Y177F/I213V/E219G had a 17.1-fold increased activity. Therefore the rFIX mutants can be used for the treatment of bleeding disorder associated with functional defects of FVIII, deficiencies of FVIII, or anti-FVIII inhibitor antibody formation.

DETAILED DESCRIPTION OF THE INVENTION

Figure 1:
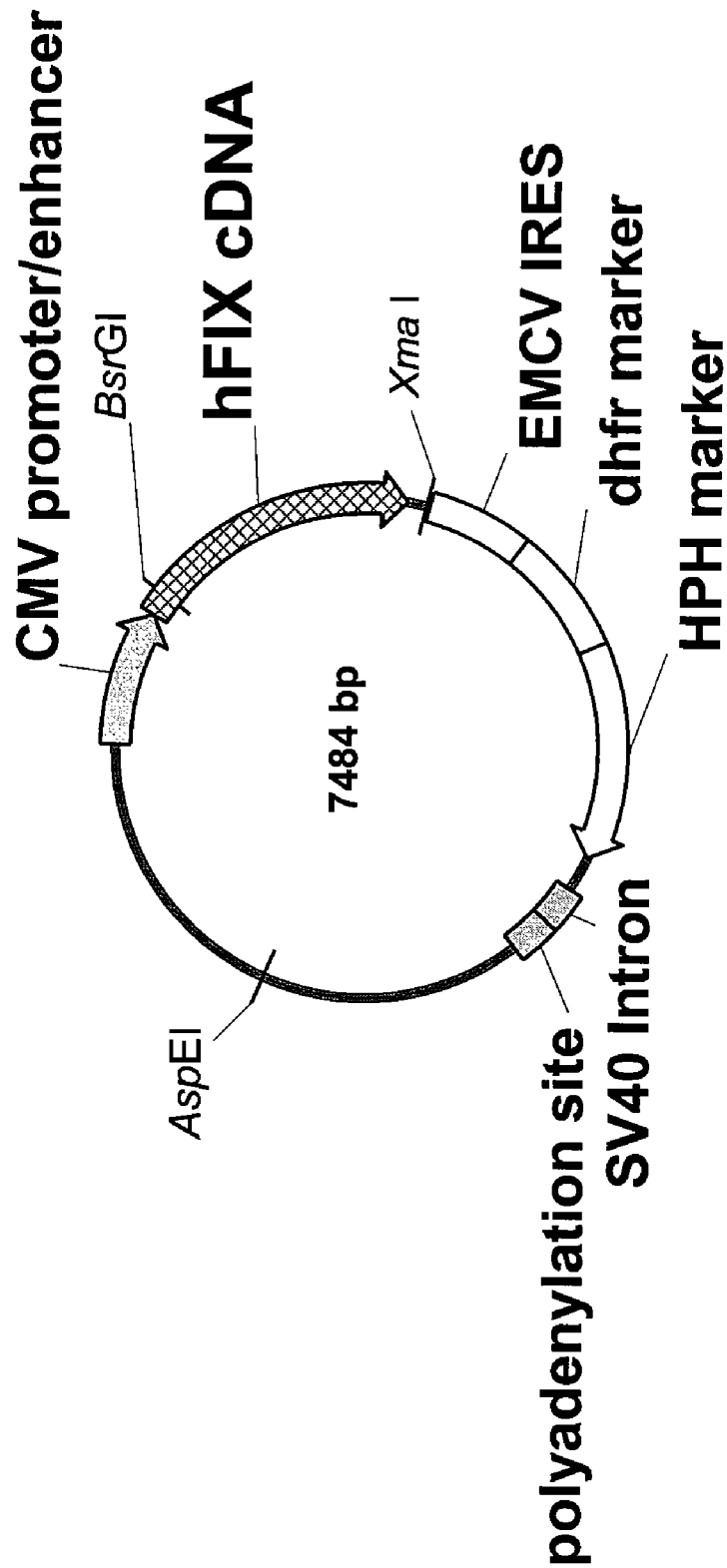
FIG. 1 shows the structure of the rFIX mutant cloning and expression vector.

The present invention relates to mutated recombinant blood coagulation FIX proteins having an improved FVIII independent FX activation potential as compared to wild type FIX (FIX-WT) or plasma derived FIX (pdFIX).

The term "amino acid" within the scope of the present invention is meant to include all naturally occurring L α-amino acids. The one and three letter abbreviations for naturally occurring amino acids are used herein (Lehninger, Biochemistry, 2d ed., Worth Publishers, New York, 1995: 71-92).

The rFIX mutant according to the present invention may be derived from any vertebrate, e.g. a mammal.

According to the present invention, the term "FIX" does not underlie a specific restriction and may include any FIX, with heterologous or naturally occurring sequences, obtained via recombinant DNA technology, or a biologically active derivative thereof. Accordingly, the term "rFIX mutant" includes any recombinant mutant derived from a FIX protein sequence of any of the foregoing FIX. Accordingly, a FIX polynucleotide or polypeptide sequence of the present invention is typically derived from a mammalian FIX sequence including, but not limited to, primate, e.g., human; rodent, e.g., rat, mouse, hamster; cow, pig, horse, sheep, or any other mammalian sequence. In one specific example of the present invention, the rFIX mutant is a recombinant mutant of human FIX. Polynucleotide and polypeptide sequences of the FIX can be found for example in the UniProtKB/Swiss-Prot Accession No. P00740. The mutated rFIX of the invention may be a mutated full length or truncated FIX. In a preferred embodiment of the present invention the mutated rFIX has a full length sequence. In the present invention the chymotrypsinogen numbering within the serine protease domain was used according to Hopfner et al. (EMBO J. 1997; 16:6626-35).

A wide variety of vectors can be used for the preparation of a rFIX mutant according to the present invention and can be selected from eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

A mutated rFIX according to the present invention may be produced by any method known in the art, for example any method applicable to non-mutated rFIX. An example was first published by Kaufman et al. (J Biol Chem. 1986; 261:9622-8). An example of a commercially available rFIX is BeneFIX® manufactured by Genetics Institute. The production of a rFIX mutant may include any method for the generation of recombinant DNA by genetic engineering, e.g. via reverse transcription of RNA and/or amplification of DNA.

A nucleic acid sequence encoding a mutant rFIX protein according to the invention may be generated by any method known in the art. Examples are polymerase chain reaction (PCR) and cloning methods. In a preferred embodiment of the present invention the DNA encoding a mutant protein of the invention is generated by in vitro mutagenesis using specific primers to generate the respective mutations.

Additionally, the recombinant DNA coding for a mutant rFIX according to the present invention, e.g. a plasmid, may also contain a DNA sequence encoding a selectable marker for selecting the cells which have been successfully transfected with the plasmid. In an example of the present invention, the plasmid may also confer resistance to a selectable marker, e.g. to the antibiotic drug hygromycin, by delivering a resistance gene, e.g. the hygromycin resistance gene conferring resistance to the marker.

The production of a rFIX mutant may include any method known in the art for the introduction of recombinant DNA into eukaryotic cells by transfection, e.g. via electroporation or microinjection. For example, the recombinant expression of human FIX mutant can be achieved by introducing an expression plasmid containing the human FIX mutant encoding DNA sequence under the control of one or more regulating sequences such as a strong promoter, into a suitable host cell line by an appropriate transfection method resulting in cells having the introduced sequences stably integrated into the genome. The lipofection method is an example of a transfection method which may be used according to the present invention.

The production of a rFIX mutant may also include any method known in the art for the cultivation of said transformed cells, e.g. in a continuous or batchwise manner, and the expression of the rFIX mutant, e.g. constitutive or upon induction. In one specific example of the present invention the nucleic acid coding for rFIX mutant contained in the host organism of the present invention is expressed via an expression mode selected from the group consisting of induced, transient, and permanent expression. Any expression system known in the art or commercially available can be employed for the expression of a recombinant nucleic acid encoding rFIX mutant, including the use of regulatory systems such as suitable, e.g. controllable, promoters, enhancers etc.

The production of a rFIX mutant may also include any method known in the art for the isolation of the protein, e.g. from the culture medium or by harvesting the transformed cells. For example, the rFIX mutant-producing cells can be identified by isolating single-cell derived populations, i.e. cell clones, via dilution after transfection and optionally via addition of a selective drug to the medium. After isolation the identified cell clones may be cultivated until confluency in order to enable the measurement of the rFIX mutant content of the cell culture supernatant by enzyme-linked immunosorbent assay (ELISA) technique. Additionally, rFIX mutant secreted by the cells may be identified for example by growing the cells in the absence of any growth promoting fetal serum or components thereof. Vitamin K is added at appropriate concentrations to improve the functional properties of the rFIX mutant protein. After identification, high rFIX mutant producing cell clones may for example be further propagated and/or stored via cryopreservation. The rFIX mutant may be also co-expressed with vitamin K reductase complex subunit 1 (VKORC1, Hallgren et al., Biochemistry 2006; 45:5587-98) and/or furin (Wasley et al. J Biol Chem. 1993; 268: 8458-65).

The host cell type according to the present invention may be any eukaryotic cell. In a preferred embodiment the cell is a mammalian cell with the ability to perform posttranslational modifications of rFIX mutant. For example said mammalian cell is derived from a mammalian cell line, like for example a cell line selected from the group consisting of SkHep-, CHO-, HEK293-, and BHK-cells. In a specific example of the present invention, the rFIX mutant is expressed in HEK293-derived cells.

There is no particular limitation to the media, reagents and conditions used for culturing the cells in the cell culture of the present invention including culturing the cells in a continuous or batch-wise manner. The cells may be cultured also under serum-free or serum- and protein-free conditions. In a specific example of the present invention the cells are cultured in a mixture of Dulbecco's modified Eagle's Medium and F-12 medium.

Additionally, the production of a rFIX mutant may include any method known in the art for the purification of rFIX mutant, e.g. via anion exchange chromatography or affinity chromatography. In one preferred embodiment rFIX mutant can be purified from cell culture supernatants by anion exchange chromatography, tandem-pseudoaffinity and affinity chromatography. The purified rFIX mutant may be analyzed by methods known in the art for analyzing recombinant proteins, e.g. the ELISA technique and by electrophoresis techniques including immuno-blotting.

The term "FVIII independent FX activation potential" as used herein means the functional activity of a rFIX mutant of the present invention and any other rFIX mutant protein which may be assessed for example by measuring activated partial thromboplastin time (aPTT).

The aPTT assays represent meaningful assays for testing the functional activity of a mutant rFIX protein because they measure the clotting time in plasma. In principle the clotting activity of any compound is determined by its addition to plasma samples and measurement of time to clotting. This can be carried out for example in plasma depleted with a protein or in plasma from inhibitor patients.

A variety of methods for an aPTT may be possible. In one preferred embodiment of the present invention the aPTT is measured in FVIII depleted plasma samples. The FVIII independent FX activation potential of a FIX mutant may be calculated in FVIII-depleted plasma as increased FVIII equivalent activity. PdFIX and FIX-WT usually have no or only a minor FVIII equivalent activity (between 0 mU/mL and 1 mU/mL). Thus any amino acid mutation leading to an increased FVIII equivalent activity as compared to pdFIX or FIX-WT can be defined as increase. In a preferred embodiment of the present invention the increased activity of a rFIX mutant is at least 2 mU/mL, and more preferably more than 5 mU/mL.

In another preferred embodiment the FEIBA equivalent activity in FVIII-inhibited patient plasma can be used for analysis of FVIII independent FX activation potential. PdFIX and FIX-WT usually have no or only a minor FEIBA equivalent activity (between 0 mU/mL and 15 mU/mL). Any increase in FEIBA equivalent activity as compared to pdFIX or FIX-WT can be defined as increase. In a preferred embodiment of the present invention the increased activity is at least 30 mU/mL, and more preferably more than 80 mU/mL.

In a further preferred embodiment the activity of a pre-activated FIX mutant protein is determined in a clotting assay in FIX-depleted plasma containing FVIII inhibitors. FIXa equivalent amounts can be calculated from clotting times of a calibration curve made with pdFIXa. In a preferred embodiment of the present invention the activity of a rFIX mutant is increased at least 10 fold and more preferably 15 fold as compared to pdFIX.

Another aspect of the present invention relates to a pharmaceutical composition comprising a rFIX mutant having a FVIII independent FX activation potential for treating a bleeding disorder associated with functional defects of FVIII or deficiencies of FVIII.

The pharmaceutical composition may further comprise an auxiliary agent, e.g. selected from the group consisting of a pharmaceutically acceptable carrier, diluent, salt, buffer, or excepient. Said pharmaceutical composition can be used for treating the above-defined bleeding disorders. The pharmaceutical composition of the invention may be a solution or a lyophilized product.

As used herein, the term "pharmaceutically acceptable" means approved by a regulatory agency of US or EU government or listed in the U.S. Pharmacopeia or other generally recognized pharmacopeia for use in animals, and more particularly in humans.

It is another object of the present invention to provide a method for treating a bleeding disorder associated with functional defects of FVIII or deficiencies of FVIII comprising the step of administering a pharmaceutical composition comprising a rFIX mutant having a FVIII independent FX activation potential to a patient in need thereof.

The expression "bleeding disorder associated with functional defects of FVIII or deficiencies of FVIII" as used herein includes bleeding disorders, wherein the cause of the bleeding disorder may be selected from the group consisting of a shortened in vivo-half-life of FVIII, altered binding properties of FVIII, genetic defects of FVIII, and a reduced plasma concentration of FVIII. Genetic defects of FVIII comprise for example deletions, additions and/or substitution of bases in the nucleotide sequence encoding FVIII whose absence, presence and/or substitution, respectively, has a negative impact on the activity of FVIII. FVIII inhibitor development may be also responsible for defects in FVIII function. In one example of the present invention, the bleeding disorder is hemophilia A.

The route of administration does not exhibit particular limitations, and in one embodiment the protein of the present invention may be administered by injection, such as intravenous, intramuscular, or intraperitoneal injection. In a preferred embodiment of the present invention the pharmaceutical composition may be administered intravenously.

The present invention will be further illustrated in the following examples, without any limitation thereto.

EXAMPLES

Example 1

Mutagenesis of FIX and Construction of FIX Expression Vectors

Publications referenced above discussing amino acid residues important for the activation of FX by FIX and own considerations were used for the construction of mutated FIX proteins. Two of the FIXa mutations are located on the 99-loop, known to contribute to substrate binding by forming the S2 and S4 substrate recognition site. The third FIXa mutation, Y177T, is placed adjacent to the S4 site. Furthermore, in FXa the 99-loop and 60-loop, both known to be highly involved in substrate recognition, are stabilized by an inter-loop interaction between the side chains of residues Y60 and K96, which might contribute to the high amidolytic activity of FXa. Exchanging Ala-95a by Lys in FIXa should yield in a salt bridge between A95aK and Glu-60 which might influence the activity of FIXa similar to that of FXa. Finally five FIX-mutants with different novel mutation combinations, i.e. SEQ ID NO:4 (FIX-Y94F/K98T), SEQ ID NO:6 (FIX-Y94F/K98T/Y177F), SEQ ID NO:8 (FIX-Y94F/A95aK/K98T/Y177F), SEQ ID NO:10 (FIX-Y94F/K98T/Y177F/I213V/E219G) and SEQ ID NO:12 (FIX-Y94F/A95aK/K98T/Y177F/I213V/E219G) were cloned in addition to SEQ ID NO:2 (FIX-WT). The respective SEQ ID NOs for the encoding nucleic acids are SEQ ID NO:3 (FIX-Y94F/K98T), SEQ ID NO:5 (FIX-Y94F/K98T/Y177F), SEQ ID NO:7 (FIX-Y94F/A95aK/K98T/Y177F), SEQ ID NO:9 (FIX-Y94F/K98T/Y177F/I213V/E219G), SEQ ID NO:11 (FIX-Y94F/A95aK/K98T/Y177F/I213V/E219G), and SEQ ID NO:1 (FIX-WT).

For the construction of the rFIX plasmids the FVIII cDNA from pCMVrFVIIIdB928/EDHPro (Herlitschka et al., J Biotechnol. 1998; 61:165-73) was replaced by human FIX cDNA. The FIX cDNA encodes a polymorphism of human FIX leading to an amino acid exchange of Thr to Ala at position 194 in the activation peptide. The vector map of the plasmid is shown in FIG. 1. A schematic of the transcription unit, containing the human cytomegalovirus (CMV) promoter/enhancer, the gene of interest (human FIX cDNA), an internal ribosomal entry site (EMCV IRES), the selection marker, the SV40 intron and the polyadenylation site is shown. The marker is a chimeric construct, consisting of the wild-type dihydrofolate reductase cDNA and the hygromycin phosphotransferase gene fused in frame.

For the construction of cDNA encoding FIX-Y94F/K98T, FIX-Y94F/K98T/Y177F, FIX-Y94F/A95aK/K98T/Y177F, FIX-Y94F/K98T/Y177F/I213V/E219G and FIX Y94F/A95aK/K98T/Y177F/I213V/E219G site-directed mutagenesis was performed using the QuickChange Site-Directed Mutagenesis Kit (Stratagene, La Jolla, Calif., USA). All PCR reactions contained 125 ng sense primer, 125 ng antisense primer (Invitrogen, Carlsbad, Calif., USA) and 5-50 ng dsDNA template, 2.5 units of PfuTurbo DNA polymerase and dNTPs in a final volume of 50 µL reaction buffer provided by the kit. After a pre-denaturation step of 1 minute at 95° C. PfuTurbo DNA Polymerase was added followed by 18 cycles of 95° C. for 30 seconds, 55° C. for 60 seconds and 68° C. for 12 minutes. The amplified product was incubated for 1 hour at 37° C. with DpnI to digest the methylated parental double stranded DNA before transformation into XL1-Blue Supercompetent Cells. For the construction of multiply mutated FIX cDNA this procedure was repeated with the according primers (Invitrogen) as shown in Table 1. The mutant FIX constructs were digested with restriction enzymes BsrGI and XmaI (New England Biolabs, Ipswich, Mass., USA) and subsequently ligated into the parental expression vector. Final FIX constructs were sequenced (Applied Biosystems Model 373A Sequencer Applied Biosystems, Foster City, Calif.) to confirm the mutations and were then linearized by AspEI for transfection.

TABLE 1

Primers for the mutagenesis of FIX constructs.

| Mutations | Sense Primer | Antisense Primer |
|---|---|---|
| Y94F-K98T | 5'-cct cac cac aac ttc aat gca gct att aat acc tac aac gac-3' (SEQ ID NO: 13) | 5'-gtc atg gtt gta ggt att aat agc tgc att gaa gtt gtg gtg agg-3' (SEQ ID NO: 14) |
| Y94F-A95aK-K98T | 5'-cct cac cac aac ttc aat aag gct att | 5'-gtc atg gtt gta ggt att aat agc ctt |

TABLE 1-continued

Primers for the mutagenesis of FIX constructs.

| Mutations | Sense Primer | Antisense Primer |
|---|---|---|
| | aat acc tac aac cat gac-3' (SEQ ID NO: 15) | att gaa gtt gtg gtg agg-3' (SEQ ID NO: 16) |
| Y177F | 5'-cac cat ctt taa caa cat gtt ctg-3' (SEQ ID NO: 17) | 5'-cag aac atg ttg tta aag atg gtg-3' (SEQ ID NO: 18) |
| I213V-E219G | 5'-ctg gaa ttg tga gct ggg gtg aag gct gtg caa tga aag gc-3' (SEQ ID NO: 19) | 5'-gcc ttt cat tgc aca gcc ttc acc cca gct cac aat tcc ag-3' (SEQ ID NO: 20) |

Example 2

Expression of Recombinant FIX Proteins

All recombinant FIX proteins were expressed in 293 human embryo kidney cells (HEK293) using plasmids containing the human FIX-WT cDNA or mutated FIX cDNA and a hygromycin selection marker.

HEK 293 cells were grown in a mixture of Dulbecco's modified Eagle's Medium and F-12 medium supplemented with 5% fetal calf serum. Transfection was performed by lipofection using Lipofectamine™2000 reagent (Invitrogen). One to 2 days before transfection HEK 293 cells were seeded on 5 cm dishes to reach a confluence of 70-80%. On the day of transfection the medium was exchanged 2 hours prior to the procedure. Six µg of FIX cDNA were transfected according to the recommended protocols. After 6 hours, fresh medium was added and the cells were cultured for 1 to 2 days before passaging into 15 cm dishes and selection of transfected cells with medium containing hygromycin at a concentration of 200 µg/mL. Two to 3 weeks later, the surviving foci were isolated into 24-well dishes in selective medium to produce stable cell lines. Each clone was grown to confluence in the presence of 5 µg/mL vitamin K1, and the secretion of FIX antigen into the medium was measured by an ELISA. FIX secreted by high-producer clones was additionally assayed in one-stage activated partial thromboplastin time assays (aPTT) and visualized on Western blots.

The best cell lines were selected for large-scale production in one-liter spinner flasks. Therefore cells were grown on 15 cm dishes to 90% confluence, trypsinized and counted in a CASY cell counter with a 150 µm capillary (Schärfe Systems, Reutlingen, Germany). 500 mL stirred spinner flasks (60 rpm) were inoculated with 106 cells/mL in 200 mL medium without fetal calf serum and supplemented with 5 µg/mL vitamin K1 and 100 µg/mL hygromycin. The medium was expanded to a final volume of 1000 mL over the next few weeks depended on the rate of growth of the cells. The culture medium was collected twice weekly. Before storage at −20° C. the culture medium was centrifuged and sterile filtrated (GP EXPRESS PLUS Membrane, SCGPT05RE, Millipore Corporation, Billerica, Miss., USA) to remove cells and debris. The supernatant contained between 0.4 and 1 µg/mL rFIX antigen. rFIX WT produced 2.6 µg/mL.

FIX antigen levels were determined by a double antibody sandwich ELISA. Therefore a sheep anti-human FIX affinity purified IgG (SAFIX-AP, Affinity Biologicals Inc., Ancaster, ON, Canada) was diluted in Tris-buffered saline (TBS, 25 mM Tris/HCl pH 7.4, 150 mM NaCl) to a concentration of 2 µg/mL and dispensed in 100 µL aliquots into the wells of a 96-well Nunc Maxisorp plate (Nunc, Roskilde, Denmark) which was then kept at 4° C. over night. The plate was washed 3 times with TBST (TBS+0.1% (v/v) Tween 20) followed by 1 hour blocking with 250 µL 3% non-fat dry milk powder (DMP) in TBS per well. The plate was then washed and 100 µL of FIX-dilution in 1% DMP in TBST were distributed in the wells. Serial dilutions of pdFIX (Enzyme Research Laboratories, South Bend, Ind., USA) were used as standard protein. The plate was incubated for 2 hours and then washed 5 times. Rabbit anti-human FIX IgG (Accurate Chemical & Scientific Corp., Westbury, N.Y., USA) was diluted in TBST/1% DMP in a ratio of 1 to 6,000 and added to each well in 100 µL aliquots for 1 hour. After 5 washing steps 100 µL of a goat anti-rabbit IgG (H+L) horseradish peroxidase (HRP)-conjugate (Bio-Rad Laboratories, Hercules, Calif., USA) diluted 1 to 3,000 in TBST/1% DMP was added and incubated for 1 hour. Unbound conjugated antibody was removed by washing the plate 5 times. The addition of 100 µL 0.4 mg/mL o phenylenediamine (OPD, Sigma, St. Louis, Mo., USA) and 0.4 mg/mL urea hydrogen peroxide in 50 mM phosphate-citrate pH 5.0 started the color development. After an incubation time of 7.5 min the reaction was stopped by the addition of 50 µL 0.5 N $H_2SO_4$. The absorbance at 492 nm was measured in an ELISA reader (Labsystems iEMF Reader MF, Vantaa, Finland).

Example 3

Purification of Recombinant FIX Proteins

FIX proteins from serum-free conditioned medium were ultrafiltrated, purified by anion exchange chromatography, tandem-pseudoaffinity and affinity chromatography and polished by inactivation and removal of preactivated rFIX. All purification steps have been carried out on the chromatographic system Äkta™Explorer 100 Air (Amersham Biosciences, Umea, Sweden) at 4° C.

The collected frozen serum-free culture medium from rFIX expression was supplemented with 2 mM benzamidine and thawed at room temperature. The pooled supernatants of each rFIX construct were concentrated on a Sartorius UDF system using a 0.7 $m_2$ polyvinylidene-difluorid (PVDF) membrane with a 10 kDa molecular weight cut off. The system was run with a flow of 330 mL/min.

Recombinant FIX was captured from culture medium by anion exchange chromatography on Q Sepharose Fast Flow in a XK26/60 column (Amersham). The matrix was equilibrated with 20 mM Tris/HCl pH 7.4 containing 0.1% Tween 80, 2 mM benzamidine and 2 mM ethylenediamine tetraacetic acid (EDTA). UDF-filtrates supplemented with 2 mM EDTA were applied to the column at a rate of 23 cm/h. The column was reequilibrated and washed with 20 mM Tris/HCl pH 7.4, 0.1% Tween 80, 200 mM NaCl, 2 mM benzamidine, 2 mM EDTA at 34 cm/h. The protein was eluted with 400 mM NaCl in equilibration buffer at the rate of 23 cm/h.

Tandem chromatography comprised a Ca2+-filtration of FIX on Q Sepharose Fast Flow in a XK26/20 column followed by pseudoaffinity chromatography on Cellufine™ Sulfate (Chisso Corporation, Tokyo, Japan) in a XK26/20 column. The columns were switched on-line at sample application and reequilibration. Washing and elution was performed with the Cellufine™ Sulfate-column alone. The samples were equilibrated with 20 mM Tris/HCl pH 7.4, 100 mM NaCl, 0.1% Tween 80, 2 mM benzamidine, and 20 mM $CaCl_2$. The elution-fraction of capture anion exchange chromatography diluted with equilibration-buffer containing 20 mM $CaCl_2$ with a conductivity of 16 mS/cm was applied onto the columns at 23 cm/h. After re-equilibration of both columns the Cellufine™ Sulfate column was washed with 20 mM Tris/HCl pH 7.4, 200 mM NaCl, 0.1% Tween 80, 2 mM benzamidine and 1 mM CaCl2. rFIX was eluted in a linear NaCl gradient from 200 to 1000 mM in washing buffer at a rate of 23 cm/h.

For affinity chromatography elution fractions of tandem chromatography were concentrated and buffer exchanged in Centriprep Ultracel YM-10 (Millipore, Bedford, Mass., USA) at 2800 g and 8° C. The retentate, supplemented with 10 mM $CaCl_2$, 40 mM $MgCl_2$ and 1 mM benzamidine, was applied to a HR 16/10 column containing a $Ca^{2+}$ dependent monoclonal antibody against human FIX light chain (American Diagnostica Inc., Stamford, Conn., USA) coupled to NHS-activated Sepharose Fast Flow (Amersham) at 38 cm/h. The matrix was equilibrated before and after sample application with 25 mM Tris pH 7.4, 150 mM NaCl, 10 mM $CaCl_2$ and 10 mM $MgCl_2$. For the next washing step the salt concentration was increased to 1000 mM NaCl. rFIX was eluted with 25 mM Tris pH 7.4, 150 mM NaCl and 20 mM EDTA at a rate of 38 cm/h. The matrix was regenerated after each chromatography run with 25 mM Tris pH 7.4, 1000 mM NaCl and 20 mM EDTA.

The removal of preactivated rFIX was achieved by incubation of rFIX-solutions with a fifteen fold molar excess of the two biotinylated inhibitors Biotinyl-ε-aminocaproyl-D-Phe-Pro-Arg-chloromethylketone (BFPRCK, Bachem, Bubendorf, Switzerland) and Biotinyl-Glu-Gly-Arg-chloromethylketone (BEGRCK, Haematologic Technologies Inc., Essex Junction, Vt., USA) over night at 4° C. FIX-Y94F/K98T was not treated with chloromethylketones.

rFIX fractions were supplemented with 0.1% ovalbumin and dialyzed in a Slide-A-Lyzer MWCO 10 kDa (Pierce, Rockford, Ill., USA) against TBS before streptavidin-sepharose (Amersham) was added in excess to the chloromethylketones. Complexes of streptavidin-sepharose with biotinylated rFIX-chloromethylketones were formed at 4° C. These complexes were removed by 10 minute centrifugation at 4000 g and 4° C.

Example 4

Western Blot Analysis of Recombinant FIX Proteins

Figure 2:
FIG. 2 shows a SDS-PAGE and Western Blot analysis of mutated rFIX proteins.

For Western blot analysis approximately 800 ng of proteins were separated by a 4-20% sodium dodecylsulfate polyacrylamide gel electrophoresis (SDS-PAGE). Gels were either stained with Coomassie solution (FIG. 2A) or electro-blotted at 0.8 mA/cm2 for 60 minutes to a Hybond-C-Extra nitrocellulose membrane using a Hoefer TE77 SemiPhor Semi-Dry Transfer Unit (Amersham). For the detection of FIX and fragments of FIX a 1:6,000 dilution of rabbit anti-human FIX IgG (Accurate Chemical & Scientific Corp., Westbury, N.Y., USA) as first antibody and a 1:3,000 dilution of goat anti-rabbit IgG (H+L) HRP-conjugate (Bio-Rad Laboratories) as secondary antibody were used. Visualization was done with AP Conjugate Substrate Kit containing a premixed BCIP/NBT solution (Bio-Rad Laboratories) according to the manufacturers protocol (FIG. 2B). Lane 2: rFIX-WT, lane 3: FIX-Y94F/K98T; lane 4: FIX-Y94F/K98T/Y177F; lane 5: FIX-Y94F/A95aK/K98T/Y177F; lane 6: FIX-Y94F/K98T/Y177F/I213V/E219G; lane 7: FIX-Y94F/A95aK/K98T/Y177F/I213V/E219G; lane 8: pdFIX; lane 1: molecular mass standard (the molecular weight is indicated in kDa). In addition of the bands of FIX, FIXα and the heavy chain (HC) and light chain (LC) of FIXaβ are also visible.

Example 5

FX Activation by FIXa

FX was activated in 25 mM Hepes pH 7.35 with 175 mM NaCl containing 1 mg/mL human serum albumin, 5 mM $CaCl_2$ and 10 μM phospholipid (PL) vesicles (phosphatidylcholin/phosphatidylserine, 60/40). PL vesicles were prepared from synthetic PLs (Avanti Polar Lipids, Alabaster, Ala., USA) by extrusion in 20 mM Tris/HCl pH 7.4, 50 mM NaCl, and 5% saccharose. The average vesicle size was 260 nm. After 15 minutes pre-incubation of 130 μL FIXa (6 nM) in reaction buffer with PL vesicles at 37° C. the reaction was started by addition of 20 μL FX in various concentrations (0 to 120 nM). Ten μL subsamples were drawn from 2.5 to 25 minutes and the reaction was terminated for 15 minutes in 200 μL buffer containing EDTA and Clone HIX-5, a monoclonal anti-human FIX purified antibody (Accurate Chemical & Scientific Corp., Westbury, N.Y., USA). The amount of FXa generated was determined spectrophotometrically with a Tecan Spectrofluor Plus micro-well plate reader (Tecan, Männedorf, Switzerland) at 405 nm for 30 minutes employing S 2765 substrate (Chromogenix—Instrumentation Laboratory, Milano, Italy) by adding 800 nM substrate to the stop-reaction-mixture.

To analyze if binding of FVIIIa to a mutant FIXa protein can neutralize the effect of the FIX mutations FX activation was also measured in the presence of FVIIIa. Ten nM Recombinate Antihemophilic Factor (Baxter, Thousand Oaks, Calif., USA) was incubated with FIXa and 4 minutes before the FX activation was started, and 10 nM thrombin (Enzyme Research Laboratories, South Bend, Ind., USA) was added. FIXa concentration was then 0.01 nM and the substrate was supplemented with 1 μM Pefabloc TH (Pentapharm, Basel, Switzerland) to prevent cleavage of the substrate by thrombin. FXa formation was quantified as described above by taking subsamples from 20 to 110 seconds.

Figure 3:
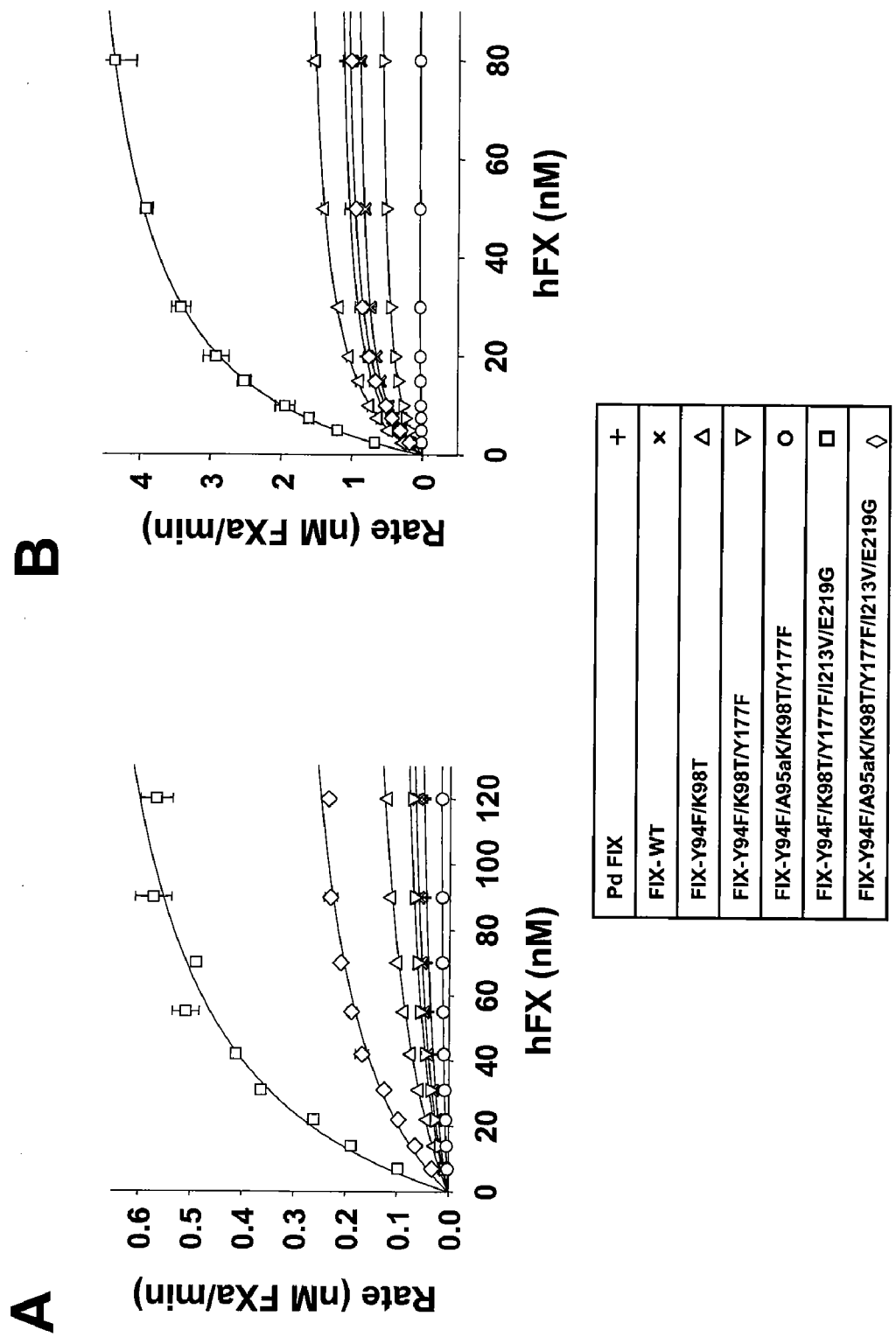
FIG. 3 shows the FX activation by mutated rFIXa proteins.

FIG. 3 shows the FX activation by a FIXa protein (pdFIX, FIX-WT and the 5 mutated proteins) in the absence (3A) and in the presence of FVIIIa (3B). Apparent KM and kcat for FX activation without addition of FVIIIa were then calculated and shown in Table 2.

As compared to pdFIX the double mutant FIX-Y94F/K98T showed a two-fold increase whereas FIX-Y94F/K98T/Y177F/I213V/E219G and FIX-Y94F/A95aK/K98T/Y177F/I213V/E219G enhanced the kcat by a factor of 17 and 6, respectively. FIX-WT and FIX-Y94F/K98T/Y177F activated FX at the same rate as pdFIXa.

TABLE 2

Kinetic parameters for FX activation without the addition of FVIIIa.

|  | KM (nM) | kcat ($10^{-3}$ $min^{-1}$) | kcat/KM ($10^{-6}$ $nM^{-1}$ $min^{-1}$) |
|---|---|---|---|
| pdFIX | 65 | 13 | 195 |
| FIX-WT | 68 | 17 | 252 |
| FIX Y94F/K98T | 83 | 35 | 425 |
| FIX-Y94F/K98T/Y177F | 68 | 20 | 293 |
| FIX-Y94F/A95aK/K98T/Y177F | 73 | 4 | 57 |
| FIX-Y94F/K98T/Y177F/I213V/E219G | 40 | 133 | 3296 |

TABLE 2-continued

Kinetic parameters for FX activation without the addition of FVIIIa.

| | KM (nM) | kcat ($10^{-3}$ min$^{-1}$) | kcat/KM ($10^{-6}$ nM$^{-1}$ min$^{-1}$) |
|---|---|---|---|
| FIX-Y94F/A95aK/K98T/Y177F/I213V/E219G | 55 | 61 | 1094 |

Addition of FVIII to the assay expectedly neutralized the FX activating effect. In contrast to the FIX mutants FVIIIa stimulated FX activation by pdFIXa was 52400-fold, whereas FX activation of FIX-Y94F/K98T, FIX-Y94F/K98T/Y177F, FIX-Y94F/K98T/Y177F/I213V/E219G and FIX-Y94F/A95aK/K98T/Y177F/I213V/E219G was reduced to approximately 29100-, 16400-, 9600- and 8400-fold, respectively (Table 3).

TABLE 3

Kinetic parameters for FX activation with the addition of FVIIIa.

| | KM (nM) | kcat (min$^{-1}$) | kcat/KM (nM$^{-1}$ min$^{-1}$) | ratio kcat/KM +/− FVIIIa |
|---|---|---|---|---|
| pdFIX | 13 | 131 | 10 | 52,430 |
| FIX-WT | 11 | 102 | 9 | 36,695 |
| FIX-Y94F/K98T | 15 | 180 | 12 | 29,122 |
| FIX-Y94F/K98T/Y177F | 14 | 68 | 5 | 16,424 |
| FIX-Y94F/A95aK/K98T/Y177F | 20 | 7 | 0 | 5,705 |
| FIX-Y94F/K98T/Y177F/I213V/E219G | 17 | 528 | 32 | 9,581 |
| FIX-Y94F/A95aK/K98T/Y177F/I213V/E219G | 13 | 122 | 9 | 8,354 |

Example 6

Clotting Assays of FIX Proteins in Plasmatic Samples

Clotting assays, i.e. aPTT assays in plasmatic samples represent meaningful assays for testing the functional activity of a mutant rFIX protein. Therefore pdFIX, rFIX-WT and rFIX mutants were serially diluted from 5 to 0.25 μg/mL in imidazol buffer containing 1% albumin (Baxter). Fifty μL of these samples, 50 μL of plasma and 50 μL of STA-APTT reagent (Diagnostica Stago, Asniéres, France) were mixed and incubated at 37° C. for 4 minutes. 50 μL of 25 mM CaCl$_2$ were added and time to clot formation was determined in an ACL10000 (Instrumentation Laboratory, Milano, Italy).

For experiments with FVIII depleted plasma (Dade Behring, Marburg, Germany) serial dilutions of FVIII Immunate (Baxter) were used as standards. FVIII inhibited patient plasma was from George King (Overland Park, Kans., USA).

Figure 4:
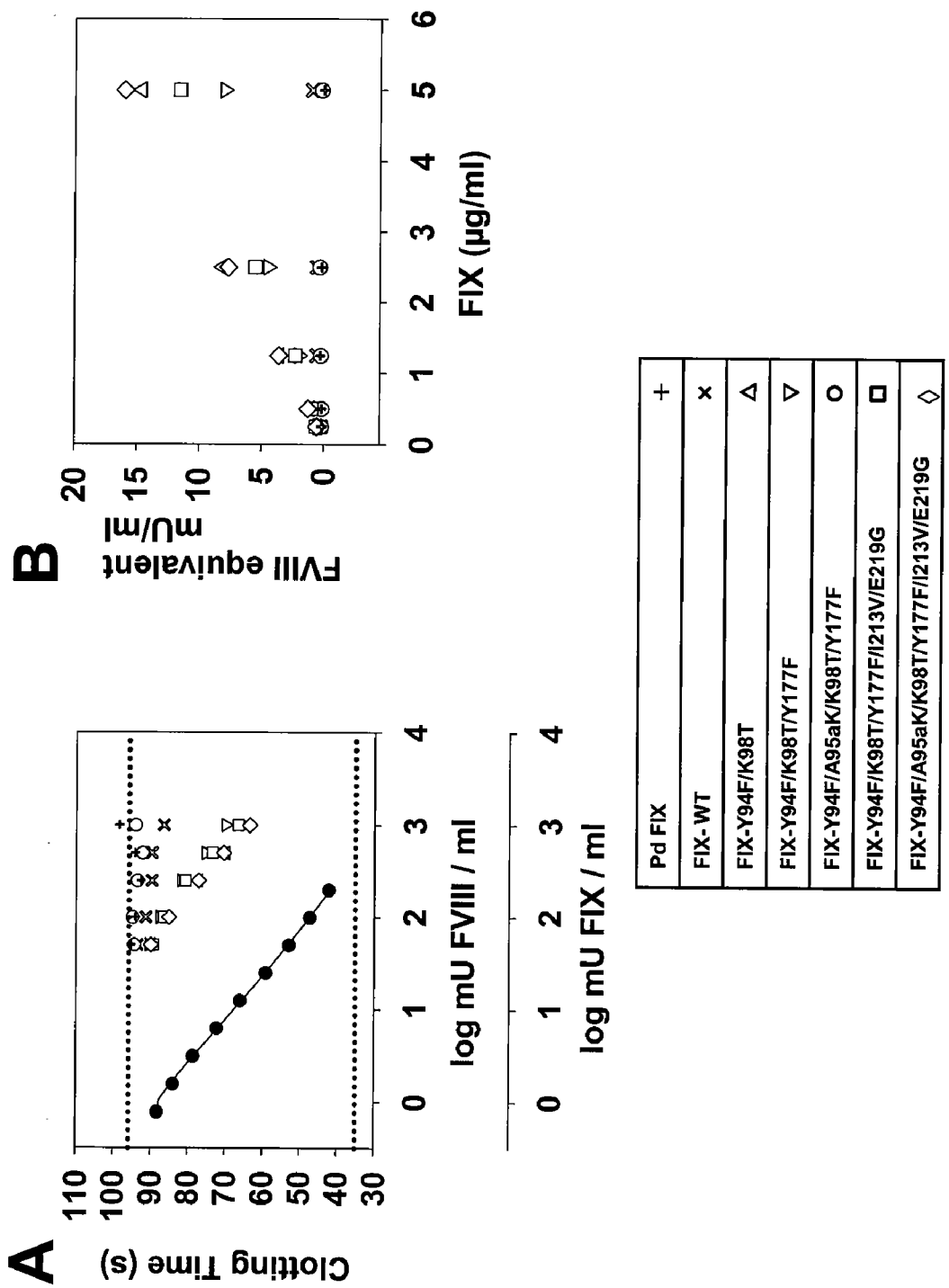
FIG. 4 shows the aPTT assay of mutated rFIX proteins in FVIII-depleted plasma.

FIX proteins were first tested in FVIII-depleted plasma (FVIII levels below 1%). Addition of FIX-WT and pdFIX to the plasma resulted in no significant shortening of clotting time. However, all mutant FIX proteins showed a concentration dependent decrease of clotting time. Five μg/mL FIX proteins reduced the clotting time from 96 seconds to 64, 70, 67 and 64 seconds for FIX-Y94F/K98T, FIX-Y94F/K98T/Y177F, FIX-Y94F/K98T/Y177F/I213V/E219G and FIX-Y94F/A95aK/K98T/Y177F/I213V/E219G, respectively (FIG. 4A). Clotting time of normal plasma (36 seconds) and that of FVIII-depleted plasma (96 seconds) are indicated by dotted lines. The FVIII Immunate standard titration, fitted to a four-parameter algorithm, is shown on the lower part of FIG. 4A. FVIII equivalent units (FIG. 4B) were calculated according to the FVIII Immunate calibration (0.78-200 mU/mL).

From the 5 mutated proteins FIX-Y94F/K98T and FIX-Y94F/A95aK/K98T/Y177F/I213V/E219G had the greatest effect with 14.7 and 16 FVIII equivalent mU/mL (Table 4), and the five-fold mutant FIX-Y94F/K98T/Y177F/I213V/E219G resulted in 12 FVIII equivalent mU/mL.

Figure 5:
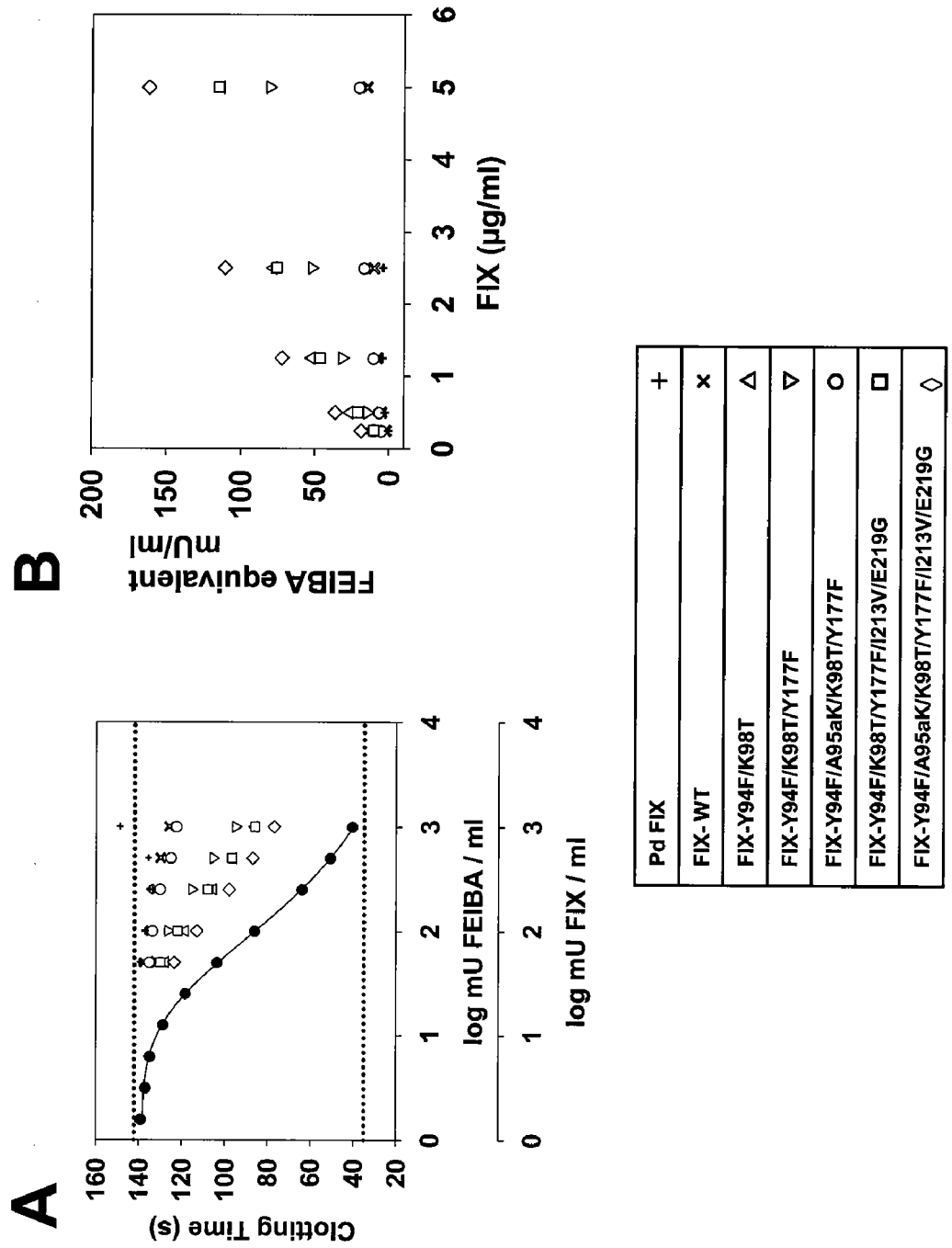
FIG. 5 shows the aPTT assay of mutated rFIX proteins in FVIII inhibited patient plasma.

An aPTT assay in FVIII-inhibited patient plasma is the most relevant assay because it indicates for the function of the mutant FIX proteins in Hemophilia A patients with FVIII inhibitors. Because FEIBA is a possible treatment for these patients, reduced clotting times of FIX proteins were compared to a standard curve of a FEIBA titration (0-1,000 mU/mL). One U/mL FEIBA restores the clotting time of normal blood in inhibitor patient plasma (approximately 36 seconds). FIG. 5 shows the results of the aPPT of pdFIX, FIX-WT and the 5 mutated proteins. Clotting time of normal plasma (36 seconds) and that of FVIII inhibitor patient plasma (142 seconds) are indicated by dotted lines. The FEIBA standard titration, fitted to a 4-parameter algorithm, is shown on the lower part of FIG. 5A. FEIBA equivalent units (FIG. 5B) were calculated according to the FEIBA calibration (1.56-1,000 mU/mL).

The best mutant rFIX protein FIX-Y94F/A95aK/K98T/Y177F/I213V/E219G showed a FEIBA equivalent activity of 162 mU/mL (Table 4). FIX-Y94F/K98T and FIX-Y94F/K98T/Y177F/I213V/E219G had both activities of approximately 115 FEIBA equivalent mU/mL.

TABLE 4 aPTT of FIX proteins in FVIII-depleted plasma (FVIII-DP) and FVIII-inhibited patient plasma (FVIII-IP).

| 5 μg/mL | FVIII-DP FVIII-equ. (mU/mL) | FVIII-IP FEIBA equ. (mU/mL) |
|---|---|---|
| pdFIX | 0.0 | inhibitory |
| FIX-WT | 1.0 | 15 |
| FIX-Y94F/K98T | 14.7 | 114 |
| FIX-Y94F/K98T/Y177F | 8.0 | 81 |
| FIX-Y94F/A95aK/K98T/Y177F | 0.2 | 20 |
| FIX-Y94F/K98T/Y177F/I213V/E219G | 11.6 | 115 |
| FIX-Y94F/A95aK/K98T/Y177F/I213V/E219G | 16.0 | 162 |

Example 7

Clotting Assays of Activated FIX Proteins in FIX-Depleted Plasmatic Samples Containing FVIII Inhibitors In the clotting assay described above FIX is directly activated by FXIa before it can activate FX. A poor activity of a rFIXa mutant in the clotting assay could therefore reflect impaired activation by FXIa or a low activity in FX activation. To further investigate the FX activation potential of the rFIX mutants without an influence of activation rates by FXIa the clotting activity of the pre-activated rFIX mutants was determined in clotting assays in FIX-depleted plasma containing FVIII inhibitors. For activation pdFIX and rFIX mutants were diluted to 25 μg/mL in TBS containing 5 mM CaCl$_2$ and 0.1% ovalbumin. FIX activation was started by the addition of pdFXIa at a molar enzyme substrate ratio of 1 to 500 at 37° C.

FXIa was removed with affinity purified goat anti-FXI IgG bound to protein G sepharose.

APTT was measured at concentrations of FIXa proteins between 0.0625 and 1 μg/mL. 50 μL FIX-depleted plasma containing FVIII-inhibitors (goat anti FVIII, 150 BU/mL) and 50 μL of the respective activated FIX proteins (0-1 μg/mL) were mixed with 50 μL aPTT-reagent for 1 minute at 37° C. Clotting time measurement was started by addition of 50 μL 25 mM $CaCl_2$. A titration with pdFIXa standard (0.0625-40 μg/mL), fitted to a four-parameter algorithm, is shown in black. Black dotted lines show clotting times of FIX-depleted and FVIII-inhibited plasma and of normal plasma.

Figure 6:
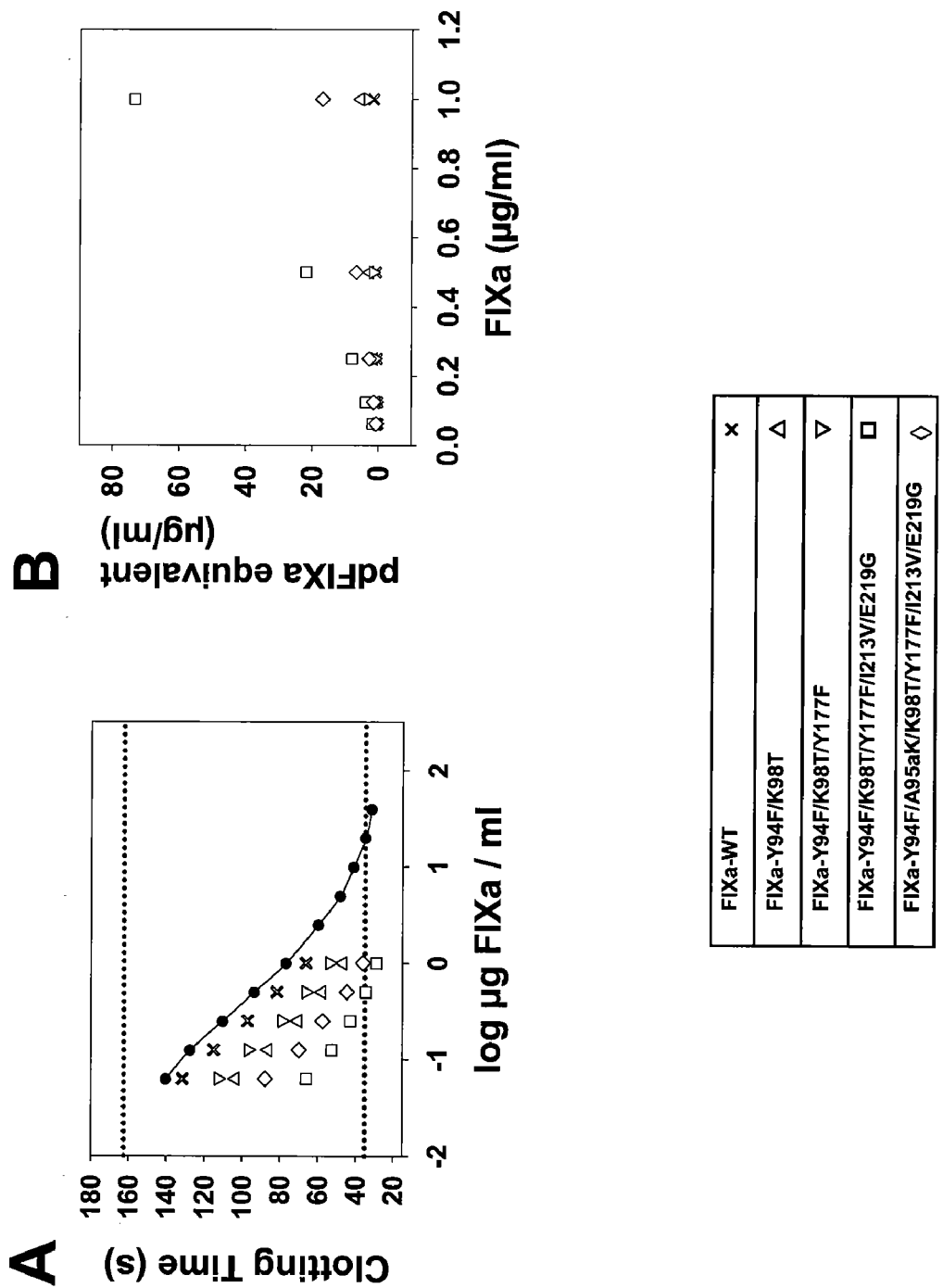
FIG. 6 shows the aPTT assay of activated mutated rFIX proteins in FIX depleted and FVIII inhibited plasma.

20 μg/mL pdFIXa restored clotting time to that of normal plasma. All activated rFIXa proteins were more efficient than pdFIXa and reduced clotting times in a concentration-dependent manner (FIG. 6A). To reach the clotting time of normal plasma 1 μg/mL of FIXa-Y94F/A95aK/K98T/Y177F/I213V/E219G and only 0.5 μg/mL FIXa-Y94F/A95aK/K98T/Y177F were necessary. For a better comparison, FIXa equivalent amounts were calculated from clotting times of a calibration curve made with pdFIXa. At 1 μg/mL FIXa-Y94F/K98T/Y177F/I213V/E219G displayed 73.4 times the activity of pdFIXa, whereas FIXa-Y94F/A95aK/K98T/Y177F/I213V/E219G had a 17.1-fold increased activity (FIG. 6B). Table 5 shows the pdFIXa equivalent activity given for 0.5 μg/mL of FIXa proteins.

TABLE 5

APPT of activated pdFIX and rFIX proteins in FIX-depleted plasma containing FVIII inhibitors.

|  | (μg/mL pdFIXa activity) |
|---|---|
| pdFIXa | 1.7 |
| FIXa-Y94F/K98T | 5.3 |
| FIXa-Y94F/K98T/Y177F | 3.4 |
| FIXa-Y94F/A95aK/K98T/Y177F | nd |
| FIXa-Y94F/K98T/Y177F/I213V/E219G | 43.6 |
| FIXa-Y94F/A95aK/K98T/Y177F/I213V/E219G | 14.4 |

This invention shows for the first time that a rationally designed rFIX mutant can substitute for FVIII activity in both FVIII depleted and FVIII inhibitor plasma. Therefore a rFIX mutant according to the present invention can be used for treatment of a bleeding disorder associated with functional defects of FVIII or deficiencies of FVIII and especially as alternatives for bypassing agents for the treatment of FVIII inhibitor patients.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A recombinant blood coagulation factor IX (rFIX) mutant having factor VIII (FVIII) independent factor X (FX) activation potential, wherein the amino acid sequence of the rFIX mutant is SEQ ID NO:8 (FIX-Y94F/A95aK/K98T/Y177F) or SEQ ID NO:12 (FIX-Y94F/A95aK/K98T/Y177F/I213V/E219G).

2. A mutant according to claim 1, wherein the amino acid sequence of the rFIX mutant is encoded by the nucleic acid sequence SEQ ID NO:7 (FIX-Y94F/A95aK/K98T/Y177F) or SEQ ID NO:11 (FIX-Y94F/A95aK/K98T/Y177F/I213V/E219G).

3. A pharmaceutical composition comprising a rFIX mutant according to claim 1.

4. A method for treating a bleeding disorder associated with functional defects of FVIII or deficiencies of FVIII, comprising the step of administering a pharmaceutical composition according to claim 3 to a patient in need thereof.

5. A method according to claim 4, wherein the bleeding disorder associated with functional defects of FVIII or deficiencies of FVIII is hemophilia A.

6. The method according to claim 4, wherein the bleeding disorder associated with functional defects of FVIII or deficiencies of FVIII is derived from the development of FVIII inhibitor antibodies.

7. A mutant according to claim 1, wherein the amino acid sequence of the rFIX mutant is SEQ ID NO:8 (FIX-Y94F/A95aK/K98T/Y177F).

8. A mutant according to claim 1, wherein the amino acid sequence of the rFIX mutant is NO:12 (FIX-Y94F/A95aK/K98T/Y177F/I213V/E219G).

9. A pharmaceutical composition comprising the mutant according to claim 7.

10. A pharmaceutical composition comprising the mutant according to claim 8.

* * * * *